United States Patent [19]

Wolf

[11] Patent Number: 5,291,898
[45] Date of Patent: Mar. 8, 1994

[54] BREATH ALCOHOL DEVICE

[75] Inventor: Karl P. W. Wolf, Webster Groves, Mo.

[73] Assignee: Alcotek, Inc., St. Louis, Mo.

[21] Appl. No.: 886,921

[22] Filed: May 22, 1992

[51] Int. Cl.$^5$ ............................................... A61B 5/08
[52] U.S. Cl. .................................. 128/719; 128/730; 422/84; 73/23.3
[58] Field of Search ................ 128/730, 719, 204.22; 73/23.3; 422/83, 84; 436/900

[56] References Cited

U.S. PATENT DOCUMENTS

| | | | |
|---|---|---|---|
| 4,274,425 | 6/1981 | Lutz et al. | 128/719 |
| 4,300,384 | 11/1981 | Wiesner et al. | 73/23.3 |
| 4,314,564 | 2/1992 | Albarda | 73/23.3 |
| 4,487,055 | 12/1984 | Wolf . | |
| 4,770,026 | 9/1988 | Wolf . | |
| 4,900,514 | 2/1990 | Fuller | 73/23.3 |
| 4,991,591 | 2/1991 | Jones et al. | 128/719 |
| 5,101,834 | 4/1992 | Wallace | 128/719 |

*Primary Examiner*—Kyle L. Howell
*Assistant Examiner*—J. P. Lacyk

*Attorney, Agent, or Firm*—Polster, Lieder, Woodruff & Lucchesi

[57] ABSTRACT

A hand held breath analyzer is energized when a mouthpiece tube is put into position. An ejector mechanism expels the mouthpiece, which de-energizes the system. The insertion of the mouthpiece not only cocks the ejector mechanism but closes a cover on an exhaust manifold of a breath sample passage. The breath sample passage includes a sample chamber with a port to receive a sampling tube fitting, and an auxiliary port. The exhaust manifold is long relative to the length of the sampling chamber and terminates in an orifice by means of which ambient air is drawn across a thermistor. The sampling tube communicates with a fuel cell chamber, into which breath is drawn by a diaphragm pump arranged, in its normal, uncocked condition, to inhibit the entrance of contaminants into the chamber. The diaphragm pump is actuated in response to operation of the thermistor, through a relay-tripped toggle linkage. A flag, connected to one of the toggle members, blocks the path of light from a photocell to a photoreceptor, insuring that the diaphragm pump is properly cocked for use before a breath sample is attempted to be taken.

32 Claims, 5 Drawing Sheets

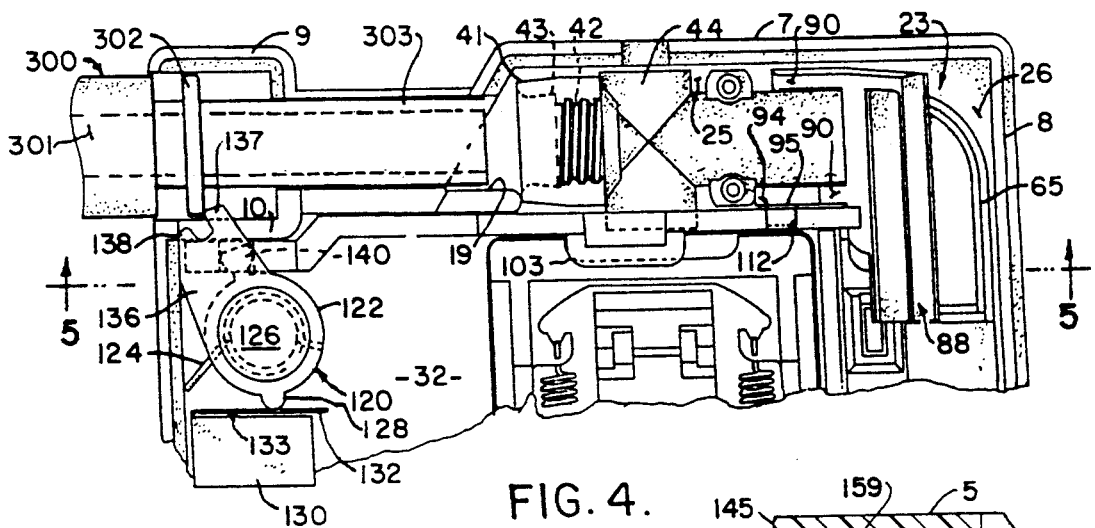
FIG. 4.
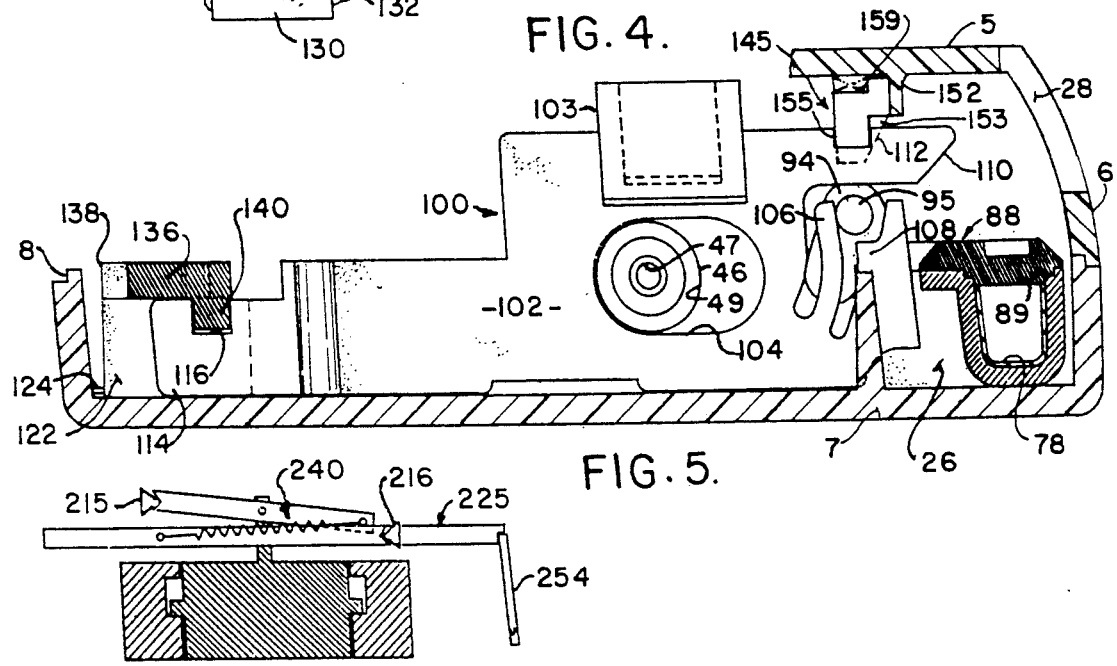
FIG. 5.
FIG. 13.
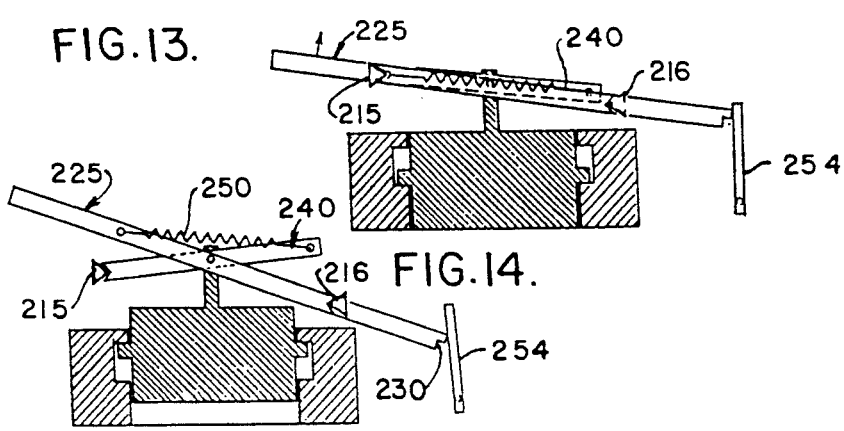
FIG. 14.
FIG. 15.

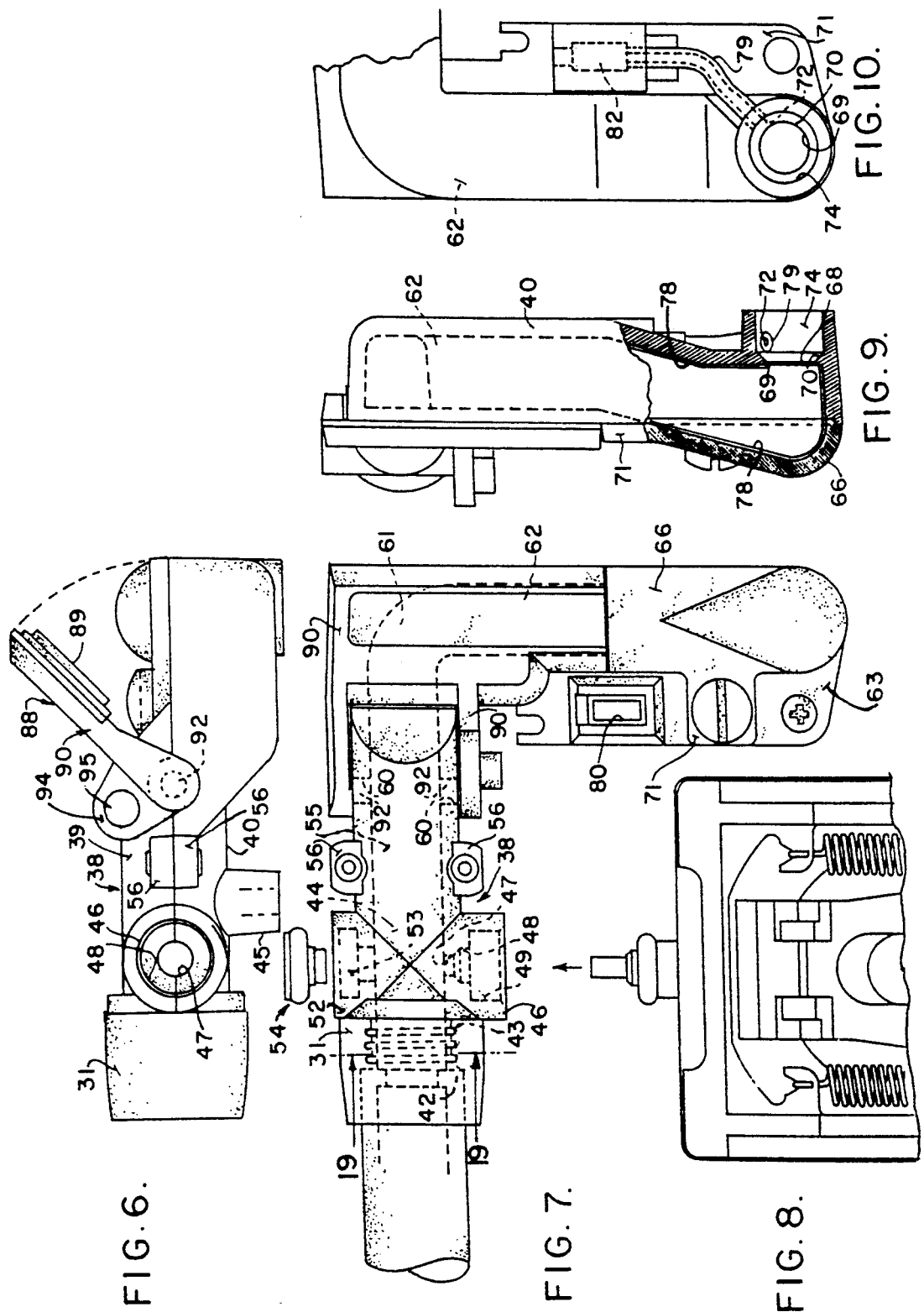

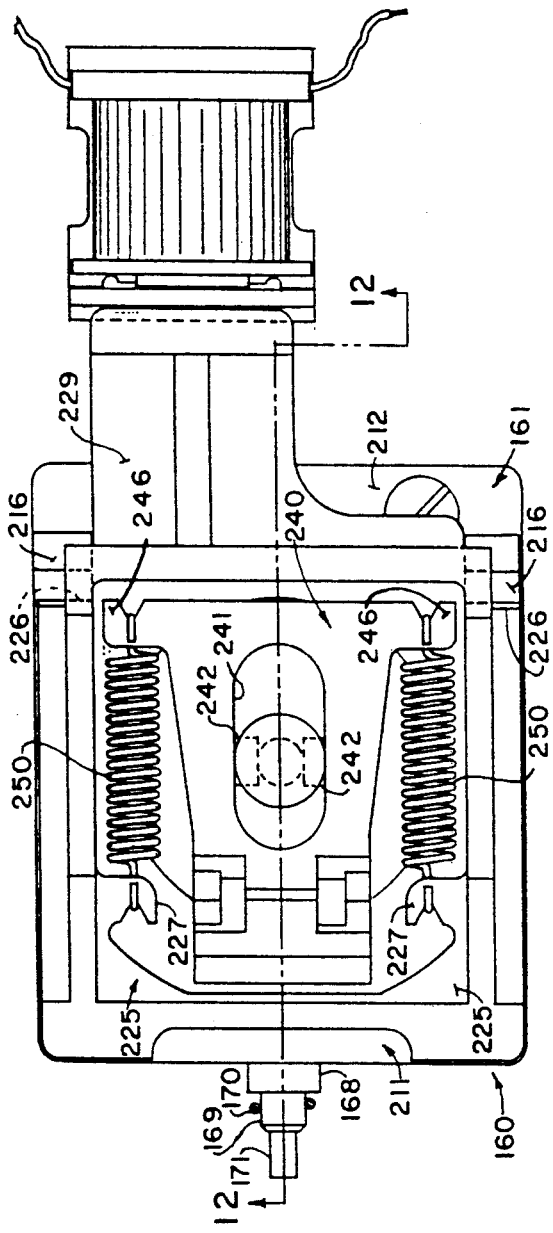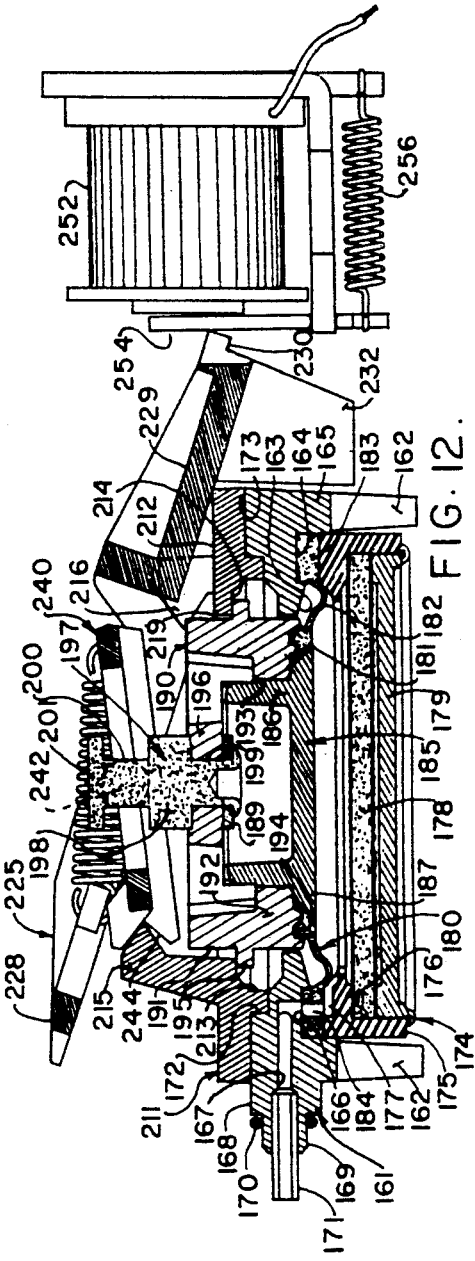

5,291,898

BREATH ALCOHOL DEVICE

BACKGROUND OF THE INVENTION

Hand held breath analyzing devices are in common use by police departments throughout the world. Such a device, with a now conventional fuel cell and pump chamber and circuit is described in Wolf U.S. Pat. No. 4,487,055, and a more detailed circuit arrangement is described in Wolf U.S. Pat. No. 4,770,026. These are merely illustrative, but their teachings are useful in understanding the present invention.

Police officers in the field are understandably somewhat reluctant to handle a mouthpiece dripping with the saliva of a suspected drunk. The breath of the subject is also likely to be loaded with moisture and contaminants that, with continued use of the device, tend to affect the operation of a thermistor in the breath path. Under field conditions, when it is likely to be dark and the weather conditions poor, it is desirable to have the operation of the device automated as much as possible, and to simplify the operation of the device from the patrolman's point of view, by minimizing the numbers of switches to operate and steps to remember. It is also desirable to insure that all the conditions precedent to the proper operation of the device be met before a sample is attempted to be taken. It is also desirable to prolong the useful life of the various elements, including the fuel cell, and to make the device as simple, rugged, and dependable as possible.

SUMMARY OF THE INVENTION

In accordance with this invention, generally stated, a hand held breath analyzing device is provided with a disposable mouth piece the insertion of which into the device cocks an ejector and energizes an electrical circuit. In the embodiment described, the insertion of the mouth piece also closes a cover on a reach of an exhaust manifold. Between an inner end of the mouth piece and the exhaust manifold, a sample chamber is provided, with fittings one of which serves to receive the sample tube of a pump and fuel cell assembly, and the other, to accommodate auxiliary equipment. At an open end of the exhaust manifold, an aspirator is provided, by which ambient air is drawn over a thermistor in response to the passage of breath past the aspirator. The breath receiving passage leading to the sample chamber, the sample chamber and the exhaust manifold are all coated with a thin film of heat-conducting material, preferably aluminum or the like. It has been found that such a layer heats quickly in response to the breath of the subject, and minimizes condensation of moisture in the travel of the breath through the breath passages. The exhaust manifold is long, relative to the length of the breath sample chamber, so that if the subject stops blowing just at the moment the sample is taken, no ambient air is mixed with the breath sample. The cover that is closed with the insertion of the mouth piece is opened in response to the ejection of the mouth piece, to permit the manifold to vent between successive uses of the device. The pump and fuel cell assembly with which the sample tube communicates at one end is of the diaphragm type, described generally in U.S. Pat. No. 4,487,055. However, in the embodiment shown and described, there is no intervening spider or other obstruction between the diaphragm and the fuel cell, the diaphragm is operated automatically in response to a signal from the breath flow thermistor, and the diaphragm is constructed to inhibit the passage of air when it is in its position nearest the surface of the fuel cell. The diaphragm is moved toward and away from the fuel cell by a toggle system that is particularly simple in construction and effective in operation. Its movement away from the surface of the fuel cell, by which the breath sample is drawn into the chamber above the fuel cell, is initiated by the retraction of a keeper from under a lip of a trip lever plate. The trip lever plate carries a depending flag, which, when the diaphragm is in its upward position, cuts the path of a light beam, which signals that the pump is not in its cocked condition, ready to use.

BRIEF DESCRIPTION OF THE DRAWINGS

In the drawings.

FIG. 4 is a fragmentary view, with the top half of the housing removed, showing part of the breath flow assembly, mouth piece in the process of being inserted, ejection mechanism, switch mechanism, and pump and fuel cell assembly;

FIG. 5 is a sectional view taken along the line 5—5 of FIG. 4, with additional parts, partly in section and partly broken away;

FIG. 6 is a view in side elevation of the breath flow assembly;

FIG. 7 is a top plan view of the assembly shown in FIG. 6, with a mouth piece, shown in fragmentary form, in place in the mouth of the breath flow assembly;

FIG. 8 is a fragmentary top plan view of a pump and fuel cell assembly;

FIG. 9 is a view, partly in section, showing the outlet leg of the exhaust manifold, and the orifice and aspirating tube;

FIG. 10 is a fragmentary bottom plan view of FIG. 7 showing a thermistor cavity communicating with the aspirator port shown in FIG. 9;

FIG. 11 is a top plan view of a pump-fuel cell assembly and trip solenoid;

FIG. 12 is a view, partly in section along the line 12—12 of FIG. 11;

FIG. 13 is a diagrammatic view showing the arrangement of elements of the over center actuator in cocked position;

FIG. 14 is a diagrammatic view showing the overcentering actuating mechanism in mid-actuating condition;

FIG. 15 is a somewhat diagrammatic view showing the over-centering elements in fully actuating position, in which the diaphragm operator is in its uppermost position;

DESCRIPTION OF THE PREFERRED EMBODIMENT

Figure 1:
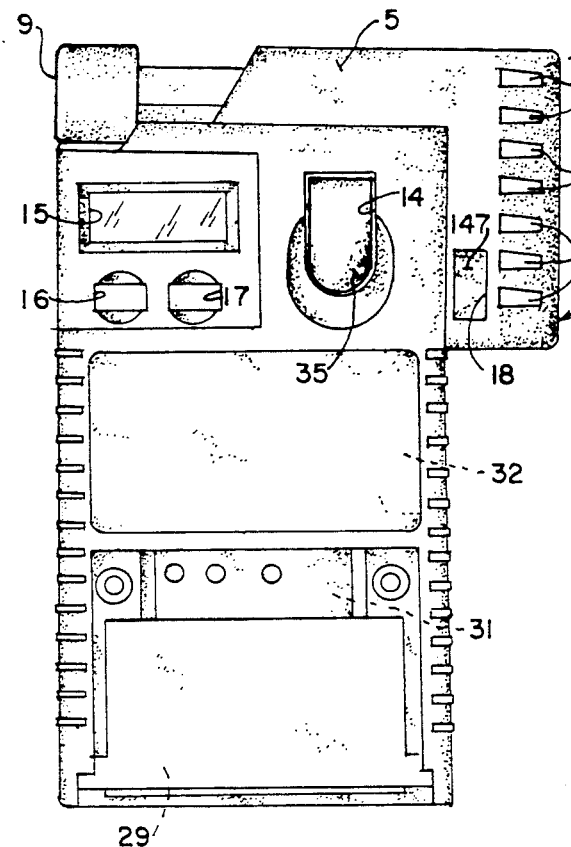
FIG. 1 is top plan view of a case or housing of one illustrative embodiment of breath analyzing device of this invention.
Figure 2:
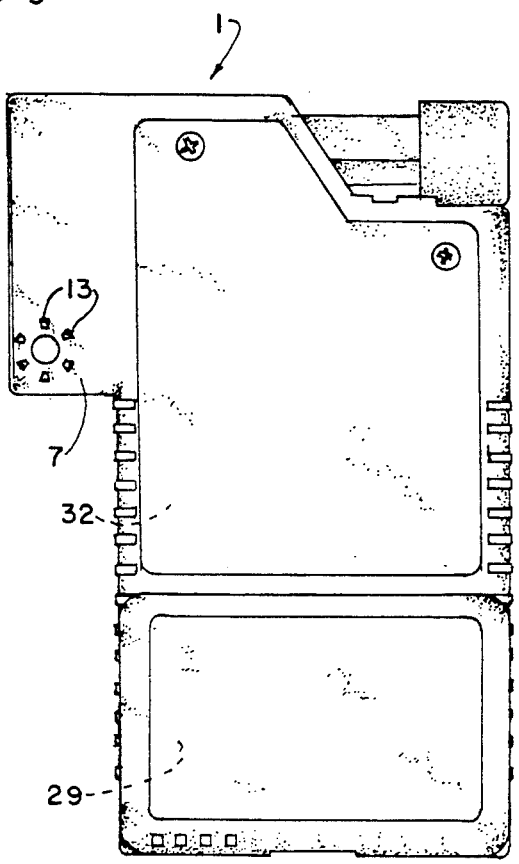
FIG. 2 is a bottom plan view of the case shown in FIG. 1.
Figure 3:
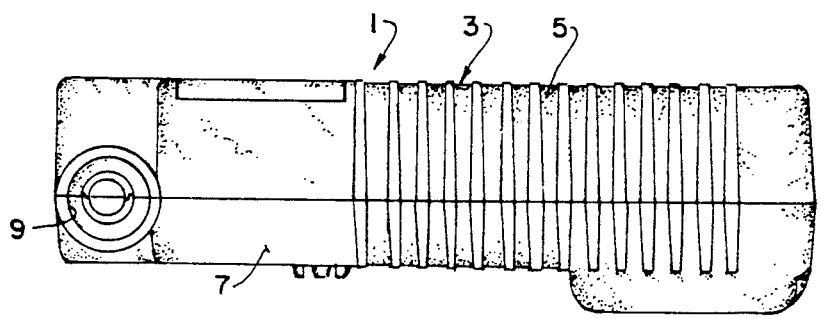
FIG. 3 is a view in side elevation viewed from left to right of FIG. 1.

Referring to the drawings for one illustrative embodiment of hand held breath analyzing device of this invention, reference numeral 1 indicates a fully assembled device. A case or housing 3 is made in two parts, an upper half 5 and a lower half 7. The upper half has a stepped rim 6, the lower half, a complementary stepped rim 8 which mates with the rim 6 when the two halves are assembled.

Figure 16:
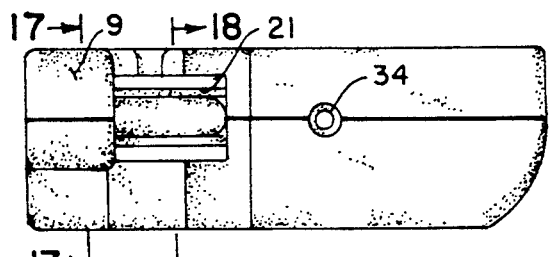
FIG. 16 is a view in top end elevation of the device shown in FIG. 1.
Figure 17:
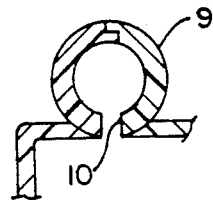
FIG. 17 is a fragmentary sectional view taken along the line 17—17 of FIG. 16.
Figure 19:
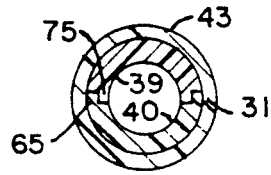
FIG. 19 is a sectional view, taken along the line 19—19 of FIG. 7.
Figure 18:
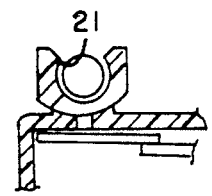
FIG. 18 is a fragmentary sectional view taken along the line 18—18 of FIG. 16.
Figure 23:
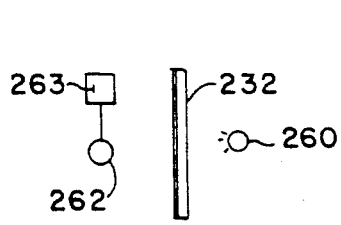

At the upper left hand corner as viewed in FIG. 1, the two halves of the housing define a mouthpiece-receiving collar 9 with an ejector slot 10 running axially along its bottom, stopping short of the outer end, as illustrated in FIGS. 4 and 19. Beyond the mouthpiece receiving collar 9, is an open topped tube guide channel 21, shown particularly in FIGS. 16 and 18, beyond which is a breath flow assembly receiving cavity 23, including a sample chamber section 25 and an L-shaped exhaust manifold section 27 with a reach axially aligned with the chamber section 23 and another, longer, reach 26 extending at substantially right angles to the sample chamber section 25. The two halves of the case also define a fitting-port 34 communicating with the sample chamber section 25. The exhaust manifold section of the upper half 5 of the housing is provided with vent slots 28 above the reach 26 after the exhaust manifold has made its bend. In its lower half 7, near the far end of the exhaust manifold section 26, is an exhaust port 11, surrounded by a circle of teeth or merlons 13, forming a crenelated wall to prevent accidental obstruction of the port 11. In the interior of the housing, a battery case area 29, a pump and fuel cell chamber, and electronic package accommodating area are provided. A set button opening 14, read-out window 15, recall button opening 16, manual button opening 17, and mouth piece ejection button opening 18 are all provided in the upper half 5 of the case, as shown particularly in FIG. 1. A cylindrical mouthpiece antechamber 19 precedes the breath flow assembly receiving cavity.

A breath flow assembly 38, shown in top plan view in FIG. 7, and in other aspects in FIGS. 4-10, is mounted in the breath flow assembly receiving cavity 23 of the housing. The main body of the breath flow assembly is made in two parts, an upper half 39 and a lower half 40, held together, in the embodiment shown, by rivets through ears 56. In this illustrative embodiment, the breath flow assembly is mounted in the case by means of a mounting boss 45 into which an anchoring screw is threaded through a hole in the case and a screw through a plate 63 that is part of the breath flow assembly, as shown in FIG. 7, extending into a boss in the case bottom. The making of the assembly in two parts makes possible the provision of a coating 78 of a heat-conductive material, such as aluminum, on the inside surfaces of a breath receiving passage, beginning with a mouthpiece end and terminating in a discharge port.

At its mouthpiece end, the two halves define a mouthpiece receiver nipple 42 around which are parallel annular ridges 43, on which a resilient mouthpiece end receiver 41 is mounted. The receiver nipple 42 communicates with a sample chamber 44. On a side of the sample chamber facing the pump-fuel cell assembly cavity, the breath sample chamber 44 is provided with a pump nipple fitting receiver 46 which includes a sample tube passage 47, a seat 48, and an O-ring well 49. Diametrically opposite the pump nipple fitting receiver 46 is an auxiliary port 52, with a stepped passage 53 to receive a plug 54. The auxiliary port 52 is aligned with the port-fitting 34 of the case. Test samples or other substances can be introduced by replacing the plug with a fitting that contains a hypodermic needle or other means of communicating with the sampling pump inlet.

Beyond the sample chamber 44, but axially aligned with it, the breath passage becomes an exhaust manifold, with a straight reach which constitutes a sample chamber extension 55, followed by an elbow section 61 and a final exhaust manifold leg 62 extending at substantially right angles to the sample chamber extension reach. The elbow section and the exhaust manifold outer leg are open along their upper edge as shown particularly in FIGS. 4 and 5. At the outer end of the leg, the exhaust manifold is offset upwardly along its lower side and covered with a domed cover 66 mounted on a web of the lower half of the assembly by a mounting tab 71 through which a screw extends into a tapped hole in a plate 63 integral with and extending from the lower half 40 of the breath flow assembly. At the outer end of the exhaust manifold, beneath the domed cover 66, the exhaust manifold opens through an aspirating orifice 68 to an open exhaust port 74. A restricting ring 69 with a flared outer side 70 produces a pressure drop as breath is blown across it, within an area at which an aspirator port 72 communicates. An aspirator tube 79 opens at the port 72 at one end, and communicates at another end with a thermistor chamber 80, open at its upper end, in which a thermistor 82 is mounted.

As has been noted, the exhaust manifold from the elbow section 61 to a wall defining the outer end of the exhaust manifold leg 62 above the port 74, is open along its upper edge. A portion of this open top is covered by the domed cover 66. The rest of the opening is closed selectively by a "clam-shell" cover 88. The cover 88 has a flat, generally rectangular section with a stepped underside 89. The steps of the cover 88 are complementary to stepped upper edges 65 of the lower half 40, which extend along both edges that mate with complementary stepped lower edges of the upper half 39, as shown in FIGS. 6, 4 and 5.

The cover 88 has spaced arms 90, projecting at right angles to a lengthwise centerline of the cover 88. The arms 90 straddle the outside surface of the sample extension 55, and have integral hinge pins 92 that are journaled into hinge pin passages 60 defined by mating semi-cylindrical passages in the upper and lower halves of the breath flow assembly. The inner of the two arms 90 has an ear 94 projecting in a direction away from the lower half of the assembly and a trunnion 95 projecting perpendicularly to the ear in a direction inwardly of the housing. It can be seen that force exerted on the trunion in a direction toward the cover will cause the cover to rotate about the hinge pins 92 to closed position, and force supplied in the opposite direction will raise the cover to the position shown in FIG. 4. To accomplish this movement, a cover actuating slide mechanism 100 is provided, best seen in FIG. 5. The cover actuating slide 100 has a central plate section 102 with a set button retainer 103 projecting upwardly from it and a nipple fitting receiver opening 104 in it. At its end nearest the trunnion pin 95, the slide is cut away to produce a closing finger 106 and a retractor finger 108, as shown in FIG. 5. The closing finger 106 engages one side of the trunnion 95; the retractor finger 108, the opposite side. The material of which the slide is made is stiffly resilient. A cover stop 110 projects over and beyond the fingers 106 and 108. A keeper notch 112 is formed in an upper edge of the slide. At an end of the slide 100 opposite the cover stop and fingers, the slide is offset from the plane of the central plate section to accommodate the mouth piece collar 9, and reduced in height to clear the ejector slot 10, as shown in FIGS. 4 and 5. An upper edge of the offset latch end 114 has formed in it a actuator lug receiver 116.

The cover actuating slide is moved between cover closing and cover opening positions by an actuator-ejector mechanism 120, which includes a barrel 122 rotatably mounted on a bearing post 126, mounted to a flat surface of the lower half 7 of the case by a screw 127. A coil spring 124 around the bearing post and within the barrel 122 serves to bias the barrel as Will be explained. The barrel Carries a switch cam 128 that operates a switch lever 132 which in turn depresses and releases a switch operator 133.

The barrel carries a generally radially extending fork 136 with prongs 137 and 138. The prong 137 projects through the ejector slot 10 at all times. The prong 138 lies clear of the interior of the mouthpiece receiving collar 9 when the fork 136 is in the position shown in FIG. 4, but moves into the confines of the collar 9 when the barrel is rotated. Inboard of the fork 136, the barrel carries a drive lug 140, shown particularly in FIGS. 4 and 5, which extends into the receiver 116 in the end 114 of the slide 100, as shown in FIGS. 4 and 5.

Figure 21:
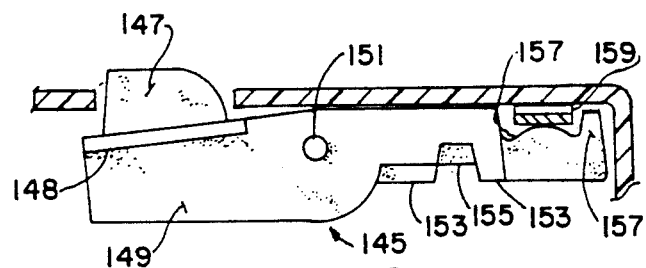
FIG. 21 is a view, partly in section and partly broken away, showing, in side elevation, a slide catch and release mechanism.
Figure 20:
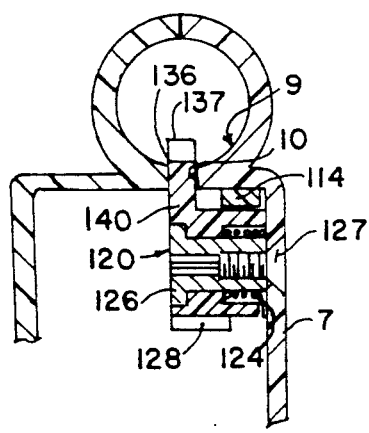
FIG. 20 is a sectional view, somewhat enlarged, taken along a line transverse of the collar 9 and through the center of the barrel 122 as viewed in FIG. 4.
Figure 22:
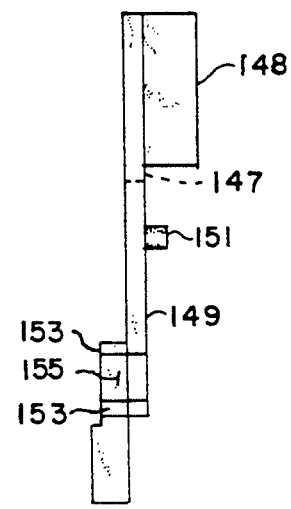
FIG. 22 is a bottom plan view of the slide catch and release mechanism of FIG. 21.

A slide catch and release mechanism 145, shown in FIGS. 21 and 22, is mounted in the case upper half 5 substantially perpendicularly to the plane of the central plate section 102 of the slide 100. The mechanism 145 includes a push button 147 that projects through the opening 18 in the case from a platform 148 which limits its upward movement, a pivot plate 149 that carries a pivot pin 151, journaled in a bracket 152 that is secured to the underside of the upper half 5 of the case 3. Integral with the pivot plate, near an end opposite from the button 147, a pair of spaced buttresses 153 have between them a latch blade or pawl 155. Beyond the outer of the buttresses 153 is a section 157 that has an arcuate profile upon which a leaf spring 159, mounted at one end on the case, bears, to bias the latch blade 155 away from the case toward the slide 100. The latch blade 155 is arranged to move into and out of the keeper notch 112 of the cover actuating slide 100. The mechanism 145 is supported against lateral movement by a wall integral with the upper half of the case 3, and the bracket 152.

The latch blade 155 is so positioned with respect to the trunnion 95 that it snaps into the keeper notch 112 only when the slide 100 has moved toward the cover 88 far enough to close the cover and to deflect the finger 106 sufficiently to maintain a downward bias on the cover 88 while the slide 100 is in its latched or cocked position with the latch blade 155 seated in the keeper notch 112.

A pump and fuel cell assembly 160 is mounted in the pump and fuel cell assembly compartment of the lower half 7 of the case. The pump and fuel cell assembly includes a center housing section 161, which is generally rectangular in plan, and from which mounting legs or bosses 162 extend. The center section 161 has a circular opening in it defined by a radially inwardly projecting ledge 163 with a substantially flat upper surface. On its underside, the ledge 163 has an annular channel 164, defined on its radially outer side by a depending cylindrical wall 165. An axial passage 166 opens into the channel 164 and communicates with a radial passage 167 that extends through a circular neck 168, a nipple 169 on which an O-ring 170 is mounted, and a sample tube 171. Above the ledge 163, and radially outwardly of it, is an annular step 172 beyond which is a planar upper surface 173.

A fuel cell case 174 has a cylindrical side wall 175 defining a circular opening. A radially inwardly extending annular shoulder 176 has an open-topped groove defining a passage 177 in its upper surface. A fuel cell 178 is seated against an under surface of the shoulder 176 within the cylindrical side wall 175, and is retained in position by a fuel cell case closure 179.

A diaphragm 180 is circular in plan, with a central opening defined by a chamfered retaining section 181, a corrugated skirt section 182 and a heavy rim 183, substantially rectangular in cross section as shown in FIG. 12. The rim 183 is seated in the channel 164, and retained by an upper planar surface of the radially inwardly extending shoulder 176 of the fuel cell case. A passage 184 axially through the rim 183 communicates at one end with the passage 166, and at its other end with the passage 177.

A diaphragm retainer 185 is cup-shaped, with a cylindrical side wall 186 and a radially outwardly extending base 187, the upper ribbed surface of which is chamfered complementarily to the under side of the chamfered retaining section 181.

A diaphragm operator 190 has a cylindrical side wall 191 toward the lower end of which is a radially inwardly extending shelf 192, with a cylindrical axially extending surface 193 and a lower surface 194 that is shaped and ribbed complementarily to the shape and ribbing of the retaining section 181 of the diaphragm. On the outer surface of the wall 191, is an annular stop flange 195. Cross members or spokes 196, integral with the side wall 191 at its upper end, have a central hub, carrying a spool 197. The spool 197 has a cylindrical body section 198, a leg 199, a neck 200 and a cap 201. The leg 199 is hollow at its lower end, and the resulting rim is turned over against the underside of a metal washer 189 to retain it in the hub of the diaphragm operator, as shown in FIG. 12. As can be seen from that FIG., the cylindrical side wall 186 is press fit against the surface 193 of the diaphragm operator, so as to secure the two parts together, and also to sandwich tightly the retaining section 181 of the diaphragm between the upper surface of the base 187 and the under surface 194 of the diaphragm operator.

The position and configuration of the corrugated skirt 182 with respect to the passage 177 is such that when the diaphragm is in its lowermost position toward the fuel cell, the skirt largely blocks the passage, so as to inhibit the ingress of contaminants and the drying of the fuel cell.

A cover section 211 of the pump and fuel cell assembly completes the stationary parts of the assembly. The cover section 211 includes a top plate 212, rectangular in plan, the underside of which fits flat against the upper planar surface 173 of the center section. A circular opening, co-axial with the opening defined by the shelf 192 of the diaphragm operator and the opening defined by the ledge 163 of the center section, is defined at its lower part by a depending circular flange 213, an upperwardly inwardly sloping part that terminates in a radially inwardly extending shelf-stop 214, and a cylindrical upper wall 219.

An actuator lever pivot wedge arm 215 projects upwardly from the top plate 212 on the sample tube side of the assembly 160, and pivot Wedge trigger lever arms 216 project from the top plate 212 on the opposite side, knife edges of the pivot wedges 215 and 216 facing one another, although offset laterally.

The circular flange 213 of the cover section fits into the annular step 172 of the center housing section, and the cover section is mounted on the center housing in any suitable way. As will be seen from FIG. 12, when the pump and fuel cell assembly is fully assembled, the diaphragm operator stop flange is caged between ledge 163 and shelf 214, which accurately delimits the motion of the diaphragm operator in both directions.

In this embodiment, a pump operating mechanism includes a trip lever 225 and an actuating lever 240. The trip lever 225 is in the form of a plate with an offset trip arm 229 at one end and a setting arm or bar 228 at another, opposite end. The plate constituting the main body of the trip lever is cut away to form spring hooks 227. At the trip arm end of the lever, at the outer edges of the main body of the lever, are pivot fulcrum V grooves, which receive the knife edges of the pivot wedge arms 216. A trip lip 230 extends along the outer edge of the trip arm 229. A flag 232 projects downwardly from the trip arm 229, as shown in FIG. 12.

The actuating lever plate 240 is positioned inside the compass of the frame of the trip lever. It has a central, elongated opening 241 from opposite edges of which cylindrical trunnions 242 extend. The trunnions 242 fit in the neck 200 between a lower surface of the cap 201 and an upper surface of the body 198. At the end of the actuating lever closest to the sample tube 171, the lever is provided with pivot fulcrum troughs 244 along a bottom line of which knife edges of the pivot arm 215 extend. At the opposite edge of the plate 240, spring hooks 246 are provided, so aligned with the spring hooks 227 of the trip lever plate as to make springs 250, mounted on the hooks, parallel.

A relay coil 252 is mounted in the case. The relay coil operates a keeper-latch 254, biased in a direction away from the coil by a keeper biasing spring 256. The keeper-latch 254 is positioned to move under and support the trip lever in cocked position, in which the diaphragm is moved to a position close to the fuel cell 178, which happens automatically when the relay coil 252 is not energized and the set bar 228 is depressed to rock the trip lever about the pivot 216 and raise the trip lip 230 above the upper edge of the keeper-latch 254. When the relay coil 252 is energized, the latch 254 is withdrawn from under the trip lip 230, permitting the trip lever to move, biased by the springs 250, to the position shown in FIG. 12, which causes the actuating lever 240 to move upwardly around the fulcrum 244 to raise the spool, hence the diaphragm operator 190 and the diaphragm to its position most remote from the fuel cell. The amount of travel of the diaphragm in either direction is determined by the spacing of the underside of the shelf 214 and the upper edge of the ledge 163. The operation of the trip mechanism and actuator lever is illustrated in FIGS. 13, 14 and 15. Because the movement of the diaphragm is only on the order of 2 millimeters, the spring, as can be seen from the FIGS., moves from a position just below the center of the trunnions 242 to a point just above the trunnions, in every position being close to alignment. This arrangement moves the piston quickly between its two extreme positions, but requires only very light pressure to hold the levers when the piston is moved against its lower stop, so that little energy is required to pull the keeper 254 from under the lip 230.

The flag 232 serves to break a beam of light between a lamp, which can be a light emitting diode 260, and a photocell 262. The photocell 262 is connected to produce a signal through a circuit shown diagrammatically at 263 either to provide an indication that the device is not cocked, or to indicate that the sampling pump diaphragm has not been pulled upward to its sampling position.

The withdrawal of the keeper-latch 254 is in response to an electrical pulse timed by analyzing the signal from the thermistor 82, produced when the thermistor is cooled by the flow of air through the apirator tube 79 in respnse to the blowing of a subject of breath through the orifice 68. In practice, the keeper needs to move only about 0.7 millimeter, and its retraction requires only 15 millicoulombs from a capacitor.

In order to place the device in condition to receive a breath sample, a disposable mouthpiece assembly 300 is provided. The mouthpiece assembly 300 includes an outer section 301, shown only fragmentarily in FIG. 4, which is embraced by the lips of the subject whose breath is to be taken, and a reduced inner section 303. An annular actuating flange 302 extends around the reduced part 303 and is spaced inwardly from the outer part 300. The outer part 303 is of a diameter closely but slidably to fit within the mouthpiece receiving port collar 9 of the case, as is the flange 302. The diameter of the inner section 303 is such as to permit the mouthpiece end receiver 41 to make a resilient seal around the inner end of the section.

It is believed that the assembly of the device will be apparent to those skilled in the art from the drawings. In operation, a disposable mouthpiece 300 is inserted through the port collar 9. As it is pushed inwardly, the flange 302 engages the finger 137 of the actuator-ejector 120. Further movement of the mouthpiece toward the receiver 41 rocks the barrel 122 around the bearing post 126, causing the drive lug 140 to move the slide 100 toward the cover 88. By the time the mouthpiece is seated in the mouthpiece receiver 41, the slide has moved to the position at which the cover is closed, the finger 106 is flexed against its natural bias, and the latch blade 155 is snapped into place in the keeper notch 112. The rocking of the barrel 122 also brings the finger 138 into position on the outer side of the flange 302, so that the flange is caged between the two fingers and the mouthpiece can not be withdrawn. The rotation of the barrel 12 also moves the cam 128 to a position at which the switch lever 132 is moved, by the bias of the operator 133, away from the switch 130, Which permits the operator 133 to close the circuit energizing the circuitry of the device. A set button 35 is depressed to push down on the setting arm 228, rocking the trip lever about the pivot 216 until the latch 254 snaps under the lip 230. The device is now ready to receive a breath sample. When a subject begins blowing through the mouthpiece, the breath travels through the entire path substantially without back pressure. The back pressure created by the restricting ring 69 is not sufficient to alter the breath alcohol concentration significantly. With continued blowing, the ambient air aspirated through the tube 79, hence through the thermistor chamber 80, cools the thermistor 82 and produces an electrical signal which is proportional to the breath flow at any instant. Continuous integration of this signal provides information on the volume of breath exhaled, and when this volume assures a sample of deep lung breath, the relay coil 252 is energized, tripping the trip lever and actuating the pump to draw a sample through the sample tube 21 to the space immediately above the fuel cell.

When the breath sample has been taken, a read-out will appear in the read-out window 15. At any time after the read-out appears, the ejector button 147 can be depressed, and the bias of the spring 124 not only causes the slide 100 to move away from the cover, but causes the finger 137 to eject the mouthpiece forceably, so that the mouthpiece is ejected into a refuse container or onto the ground without the need for the officer administering the test to touch the used mouthpiece.

If the subject stops blowing just as the sample is taken, the length of the exhaust manifold is such as to preclude the induction of ambient air into the sample chamber as the sample is being taken. Because the exhaust manifold is long relative to the length of the sample chamber, it is desirable to vent as much of it as possible between successive tests. To that end, the opening of the cover 88, exposes a substantial length of the exhaust manifold to the atmosphere, for which purpose the slots 28 are provided. The coating of the interior surfaces of the breath passage with aluminum has been found to minimize condensation in the passage. This is because, although the aluminum or the like is an excellent conductor of heat, the thin coating (for example, 0.10 mils) heats to breath temperature very quickly, and thereafter precludes condensation. The breath flow assembly is preferably made of plastic, which, in cold weather, tends to remain cold, and therefore, uncoated, would lead to substantial condensation.

It might be considered that the operation of the thermistor 82 would be adversely affected by the differences in temperature of the ambient from time to time. However, the difference in the temperature gradient between the high temperature of the thermistor and the temperature of the ambient is not great within the range of temperatures at which the device is ordinarily operated, e.g., from 50 to 100 degrees Fahrenheit. At the lower ambient, the thermistor is operating at a somewhat lower temperature, at which it is a bit less sensitive to the slightly increased chilling effect of the colder air and the effect is to some extent self-compensating. In any event, the accuracy of the device is very high throughout the range of 50 to 100 degrees Fahrenheit.

Numerous variations in the construction of the device of this invention, within the scope of the appended claims, will become apparent to those skilled in the art in the light of the foregoing description. Merely by way of example, the rotating member referred to as a barrel can take the form of a plate or other shape, as long as it is provided with means for engaging the mouthpiece and is biased toward mouthpiece ejecting position. The metal coating the inside surface of the breath sample chamber and exhaust manifold can be different from aluminum, as, for example, copper, silver or gold, as long as it is unreactive with ethanol and heats quickly. Other forms of aspirators can be used, such as a true venturi. Other configurations of clam-shell cover and its arms can be used, as well as those of the slide mechanism and latch and release mechanism. Other means of mounting the various elements or of joining parts of them can be employed, as for example, adhering the parts of the breath flow assembly rather than using rivets. The device and its elements can be used in connection with the measurement of the contents of small samples of gasses different from ethanol, as for example, extracting samples of gasses from a flowing stream or quiescent volume in an industrial process, or taking samples in a living or working space, to test for carbon monoxide, formaldehyde, methane or the like. These are merely illustrative.

Having thus described the invention, what is claimed and desired to be secured by Letters Patent is:

1. In a hand-held breath analyzing device with a housing having mouthpiece tube-receiving means, the improvement comprising detent means mounted in said housing to move between engaging and disengaging positions, and spring means biasing said detent means to disengaging position, a disposable mouthpiece having a tube with an inner end adapted to be embraced by said mouthpiece tube-receiving means, an outer end through which a subject blows, and means intermediate said outer and inner ends of said tube for engaging said detent means, said detent means being displaced against the bias of said spring by movement of said mouthpiece tube into seated condition in said mouthpiece tube-receiving means, and means, responsive to said displacement, for holding said detent means in mouthpiece-engaging position with said tube and embraced by said mouthpiece tube-receiving means until said detent holding means is deliberately released, whereupon said detent means, moving with the bias of said spring means, ejects said mouthpiece from said mouthpiece tube receiving means and away from said housing.

2. The improvement of claim 1 wherein said mouthpiece tube receiving means comprises a resilient annulus of a size and shape snugly to receive said tube end.

3. The improvement of claim 1 wherein said detent comprises a rotating barrel with a finger projecting radially therefrom, said detent engaging means comprises a flange projecting from said mouthpiece tube and dimensioned and positioned to engage said finger to rotate said barrel against the bias of said spring means.

4. The improvement of claim 3 wherein the mouthpiece tube is cylindrical, circular in transverse cross section, and the flange is annular and projects radially outwardly from the tube.

5. The improvement of claim 3 wherein said rotating barrel has a second finger, spaced from said first finger to receive said flange between them when said barrel is rotated, said second fiber engaging a part of said flange to prevent outward displacement of said mouthpiece until said detent means is deliberately released.

6. The improvement of claim 1 wherein the analyzing device has a switch through which an analyzing circuit is energized and de-energized, and said detent means includes means for moving said switch to energizing position when said mouthpiece is inserted and for releasing said switch to de-energizing position when the mouthpiece tube is not in place.

7. The improvement of claim 6 wherein said detent means comprises a rotating barrel with a finger projecting radially therefrom and said means for moving said switch comprises a cam on said barrel and a spring-biased switch operator, said cam operating said switch operator to move said switch.

8. The improvement of claim 1 including a breath flow assembly of which said mouthpiece tube receiving means is a part, a breath sample chamber having a breath-passage communicating with said mouthpiece tube receiving means, and an exhaust manifold having a breath passage with a beginning communicating with the breath sample chamber breath passage at a place remote from said mouthpiece tube receiving means, said exhaust manifold breath passage being long as compared with the length of said breath sample chamber breath passage between said mouthpiece tube receiving means and the beginning of said exhaust manifold breath passage, said exhaust manifold breath passage having a clam shell cover over at least part of its length, and means for moving said cover between closed position when said mouthpiece is seated and open position when said mouthpiece is not seated.

9. The improvement of claim 8 wherein said means for moving said cover comprises a slide, and means connected to said detent means for moving said slide to cover closing position when said mouthpiece is inserted and seated and for moving said slide to cover opening position when said mouthpiece is not seated.

10. The improvement of claim 9 wherein said slide has a notch in one edge and a pawl is mounted on said housing and biased to snap into said notch when said slide is in cover closing position.

11. The improvement of claim 10 wherein said cover pivots about a hinge and carries a trunnion, offset from said hinge, and said slide carries a flexible finger that engages said trunnion to rotate said cover to closed position when said slide is moved in response to the insertion of said mouthpiece, said slide moving to a position beyond cover-closing position until said pawl moves into said notch, thereby flexing said finger against said trunnion and providing continuous bias of said cover to closed position to ensure a tight seal.

12. The improvement of claim 11 in which said finger is integral with said slide.

13. A hand-held breath analyzing device having a breath sample chamber with a breath passage through it and an exhaust manifold with a breath passage through it communicating with said sample chamber breath passage, said manifold breath passage being long as compared with the length of the breath sample chamber breath passage whereby ambient air is inhibited from reaching the breath sample chamber if a subject who is blowing into the device stops blowing at the moment of sampling from the breath sample chamber.

14. The device of claim 13 wherein a removable cover extends over at least a portion of said exhaust manifold breath passage adjacent said breath sample chamber, whereby upon opening said cover, alcohol and water vapors in said manifold breath passage can dissipate rapidly.

15. The device of claim 14 including means for automatically closing said cover when a mouthpiece is installed in said analyzing device and opening said cover when said mouthpiece is removed.

16. The device of claim 13 including restriction means near an outer end of said exhaust manifold breath passage to create a pressure drop zone as breath flows through the manifold breath passage, hence through the restriction, and wherein an open end of a tube is positioned in a lower pressure zone produced by said pressure drop zone, said tube being connected to a thermistor chamber housing a thermistor, said thermistor chamber opening to the ambient atmosphere, whereby ambient air drawn through said tube in response to lower pressure in said lower pressure zone is drawn over said thermistor when a subject blows through said manifold.

17. The device of claim 13 wherein said exhaust manifold opens to the ambient atmosphere through an opening surrounded by a crenelated guard wall.

18. The device of claim 13 wherein the breath sample chamber and exhaust manifold are made of a heat insulating material and inside surfaces thereof defining said breath sample chamber and exhaust manifold passages are coated with a heat-conductive material.

19. The device of claim 18 wherein the heat-conductive material is aluminum.

20. The device of claim 19 wherein the coating is on the order of 0.10 mils thick.

21. The device of claim 13 wherein a sample port opens into said breath sample chamber and an accessory port, spaced from said sample port, is provided, opening directly into said breath sample chamber.

22. In a hand-held breath analyzing device having a housing and a breath flow assembly including a breath sample chamber, a pump assembly having a sampling tube, said sampling tube communicating with said pump chamber, said pump assembly comprising a diaphragm and a pump chamber, and a fuel cell communicating with said pump chamber, the improvement comprising sad pump assembly being selectively mounted in said housing with said sampling tube communicating with said breath sample chamber and demounted from said housing, with said sampling tube removed from communication with said breath sample chamber.

23. In a hand-held breath analyzing device having a breath sample chamber, a pump assembly having a sampling tube communicating with said breath sample chamber, said pump assembly comprising a diaphragm and a pump chamber, and a fuel cell communicating with said pump chamber, the improvement comprising said sampling tube communicating with said pump chamber through an opening adjacent an edge of said diaphragm, said edge having an annular corrugation extending toward said tube opening, said corrugation obstructing said opening when said diaphragm is moved toward said fuel cell as far as it can.

24. In a hand-held breath analyzing device having a breath sample chamber, a sampling tube communicating with said breath sample chamber, a pump assembly communicating with said tube, said pump assembly comprising a diaphragm and a pump chamber, and a fuel cell communicating with said pump chamber, said pump assembly diaphragm being mounted in a case and being movable toward and away from said fuel cell, and means for moving said diaphragm toward and away from said fuel cell, the improvement comprising a trip lever pivotally connected to said case and to an actuating lever pivotally connected to a diaphragm hub assembly slidably mounted in said case, over-centering spring means having one end connected to said trip lever and another end connected to said actuating lever, said spring means biasing said trip lever in a direction in which said diaphragm is moved by said actuating lever away from said fuel cell, and means for selectively latching said trip lever in a position at which said diaphragm is moved by said actuating lever to its limit toward said fuel cell, means for unlatching said trip lever, and means for moving said trip lever to latched position.

25. The improvement of claim 24 wherein actuating level and trip lever pivot arms are fixed to a surface of said case and project outwardly from said case, said pivot arms having wedges with knife edges, said knife edges of said actuating lever and trip lever arms being spaced from and facing one another, said trip lever and actuating lever being pivoted to said case along said knife edges.

26. The improvement of claim 24 wherein said latching means comprise a keeper-latch biased toward said trip lever to move under an end of said trip lever when said trip lever is in said position at which said diaphragm is moved to its limit toward said fuel cell, and means for moving said keeper-latch from under said trip lever to permit the trip lever to pivot by the bias of said spring, to a position at which the diaphragm is moved by the actuating lever to its limit away from said fuel cell.

27. The improvement of claim 26 wherein the trip lever moving means is a relay coil.

28. The improvement of claim 26 including a manually operated push button connected to restore said actuating lever to latched position.

29. The improvement of claim 24 including a flag carried by said trip lever and moving with said trip lever from a position at which it blocks a light path between a source of light and a photoreceptor when said diaphragm is in its position away from said fuel cell and a position at which it does not block said path when said diaphragm is in it position toward said fuel cell.

30. In a gas sampling device having a sampling tube, a pump assembly communicating with said tube, said pump assembly comprising a diaphragm and a pump chamber having a bottom wall, said pump assembly diaphragm being mounted in a case and being movable toward and away from said bottom wall, and means for moving said diaphragm toward and away from said bottom wall, the improvement comprising a trip lever pivotally connected to a diaphragm hub assembly slidably mounted in said case, over-centering spring means connected at one end to said trip lever and at another end to said actuating lever, said spring means biasing said trip lever in a direction in which said diaphragm is moved by said actuating lever away from said bottom wall, and means for selectively latching said trip lever in a position at which said diaphragm is moved by said actuating lever to its limit toward said bottom wall, means for unlatching said trip lever, and means for moving said trip lever to latched position.

31. The device of claim 30 wherein the bottom wall comprises a fuel cell.

32. The device of claim 30 including stop means carried by said case and means carried by said diaphragm moving means for engaging said stop means as said diaphragm moves toward and away from said bottom wall, whereby the travel of said diaphragm toward and away from said bottom wall is limited by said stop means.

* * * * *